United States Patent [19]
Fujino et al.

[11] 4,382,923
[45] May 10, 1983

[54] TETRAPEPTIDE ACYLHYDRAZIDES, THEIR PRODUCTION AND USE

[75] Inventors: Masahiko Fujino, Hyogo; Mitsuhiro Wakimasu, Osaka; Kiyohisa Kawai, Kyoto, all of Japan

[73] Assignee: Takeda Chemical Industries, Ltd., Osaka, Japan

[21] Appl. No.: 311,899

[22] Filed: Oct. 15, 1981

[30] Foreign Application Priority Data

Oct. 24, 1980 [JP]   Japan ................................. 55-149848

[51] Int. Cl.³ ..................... A61K 37/00; C07C 103/52
[52] U.S. Cl. ............................... 424/177; 260/112.5 E
[58] Field of Search .................. 260/112.5 E; 424/177

[56]     References Cited
        U.S. PATENT DOCUMENTS

| | | | |
|---|---|---|---|
| 4,264,491 | 4/1981 | Smithwick, Jr. et al. ... | 260/112.5 E |
| 4,277,394 | 7/1981 | Fujino et al. ................. | 260/112.5 E |
| 4,337,247 | 6/1982 | Fujino et al. ................. | 260/112.5 E |

OTHER PUBLICATIONS

Naturwissenschaften 66, S 625 (1979), M. Fujino et al.

*Primary Examiner*—Delbert R. Phillips
*Attorney, Agent, or Firm*—Wegner & Bretschneider

[57]     ABSTRACT

Novel tetrapeptide acylhydrazides, inclusive of acid addition salts thereof, which have the formula:

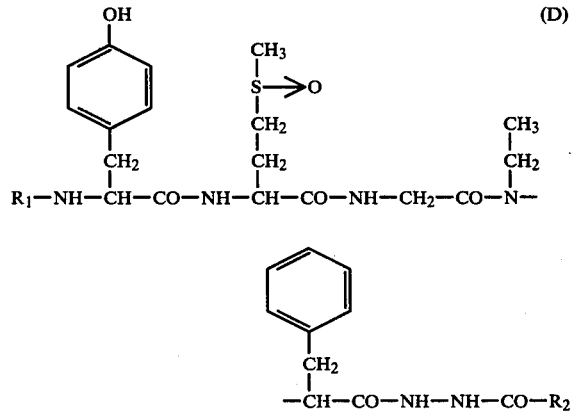

wherein $R_1$ is hydrogen or methyl, $R_2$ is lower alkyl; are useful as analgesics.

12 Claims, No Drawings

TETRAPEPTIDE ACYLHYDRAZIDES, THEIR PRODUCTION AND USE

This invention relates to new tetrapeptide acylhydrazides, a method for production of the same and an analgesic containing any of the compounds.

Hughes et al [Nature 258, 577 (1975)] isolated from the pig brain a couple of pentapeptides displaying morphinomimetic activity on intracerebral administration, i.e. enkephalins, and determined their chemical structures, i.e. H-Tyr-Gly-Gly-Phe-Met-OH and H-Tyr-Gly-Gly-Phe-Leu-OH. While these substances show morphinomimetic activity on direct intracerebral administration, they do not produce analgesic effects when administered by the intravenous route.

As another peptide-type analgesic, there has been known $\beta$-endorphin which displays an overt analgesic action even by intravenous administration. This compound, however, being a polypeptide consisting of 31 amino acid moieties, its organic synthesis is so difficult that the production thereof in a sufficient quantity for pharmaceutical use is almost impossible from an industrial viewpoint.

The present inventors investigated the possibility of securing a compound which would be economically advantageous, stable as a chemical compound and able to provide a sufficient analgesic effect on administration by the oral, intravenous or subcutaneous route. The investigation led to the discovery that certain tetrapeptide acylhydrazides are suited for the above mentioned purpose. The above finding was followed by further research which has eventually resulted in the present invention.

This invention is, therefore, directed to:
(1) A tetrapeptide acylhydrazide of the following formula (I)

(2) A method of producing a tetrapeptide acylhydrazide of the formula (I), which is characterized by subjecting a compound of the formula (II): to a reaction by which the protective group or groups can be removed.

(3) An analgesic containing a tetrapeptide acylhydrazide of formula (I) or a pharmacologically acceptable acid addition salt thereof.

In this specification, amino acids and peptides are designated either by the abbreviations commonly used in the art or by those adopted by the Committee on Chemical Nomenclaure of IUPAC-IUB. Some of such abbreviations are as follows.

Ala: alanine
Gly: glycine
Leu: leucine
Phe: phenylalanine
Met(O): methioninesulfoxide
EtPhe: N-ethyl-phenylalanine
Tyr: tyrosine
MeTyr: N-methyl-tyrosine In the following description, the comounds repeatedly referred to are designated by the following abbreviations.

DCC: N,N'-dicyclohexylcarbodiimide
HONB: N-hydroxy-5-norbornene-2,3-dicarboximide
ONB: HONB ester
Z: benzyloxycarbonyl
BOC: t-butoxycarbonyl
$Bu^t$: t-butyl
DMF: dimethylformamide
Bzl: benzyl
HOBT: N-hydroxybenzotriazole
MeOH: methyl alcohol
AcOEt: ethyl acetate
TEA: triethylamine
THF: tetrahydrofuran
TFA: trifluoroacetic acid Throughout this specification, wherever any amino acid or its residue is designated by an abbreviation in the above manner, it represents the L-form thereof unless otherwise specified, while the D-form of any amino acid or residue thereof is specified by (D)- or D-.

In the formula (I), the lower alkyl as represented by $R_2$ is preferably an alkyl or 1 to 8 carbon atoms, such as methyl, ethyl, n-propyl, isopropyl, n-butyl, isobutyl, (I)

$R_1$—NH—CH(CH$_2$-C$_6$H$_4$-OH)—CO—NH—CH(CH$_2$CH$_2$S(CH$_3$)→O)—CO—NH—CH$_2$—CO—N——CH(CH$_2$-C$_6$H$_5$)—CO—NH—NH—CO—$R_2$
                                                                (D)    (with CH$_3$ on N)

wherein $R_1$ is hydrogen or methyl, $R_2$ is lower alkyl; or a pharmacologically acceptable acid addition salt thereof.

(II)

$R_1$\N(Y$_1$)—CH(CH$_2$-C$_6$H$_4$-OY$_2$)—CO—NH—CH(CH$_2$CH$_2$S(CH$_3$)→O)—CO—NH—CH$_2$—CO—N——CH(CH$_2$-C$_6$H$_5$)—CO—NH—CO—$R_2$
                                                            (D)    (with CH$_3$ on N)

wherein $R_1$ is hydrogen or methyl; $R_2$ is lower alkyl; $Y_1$ is a protective group; $Y_2$ is hydrogen or a protective n-pentyl, isopenyl, n-hexyl, isohexyl and n-heptyl, particularly desireble is an alkyl of 1 to 5 carbon atoms.

Above lower alkyls may be substituted by hydroxyl, lower alkoxy, lower alkylthio, lower alkylthio oxide, halogen or oxo etc. There may be mentioned methoxy or ethoxy etc. as lower alkoxy, methylthio or ethylthio etc. as lower alkylthio, methylthiooxide or ethylthiooxide etc. as lower alkylthiooxide, chloride or fluoride etc. as halogen.

As examples of the protective group $Y_1$ in the above general formula, there may be mentioned benzyloxycarbonyl, t-butoxycarbonyl, t-amyloxycarbonyl, isobornyloxycarbonyl, adamantyloxycarbonyl, chloro- or nitro-substituted benzyloxycarbonyl, o-phenylthio and diphenylphosphinomethyl. The protective group $Y_2$ may for example be benzyl and t-butyl.

A peptide derivative of chemical structural formula (I) is produced by condensing an amino acid or peptide fragment capable of forming polypeptide (I) with the remaining part of the polypeptide. Thus, for example, the following alternative methods may be utilized for this purpose: The methods described in M. Bodansky and M. A. Ondetti: Peptide Synthesis, Interscience, New York, 1966; F. M. Finn and K. Hofmann: The Proteins, Vol. 2, ed. by H. Neurath, R. L. Hill, Academic Press Inc., New York, 1976; or Nobuo Izumiya et al.; Peptide Gosei (Peptide Synthesis), Maruzen Inc., 1975, may be utilized. Thus, for example, the azide method, chloride method, acid anhydride method, mixed acid anhydride method, DCC method, active ester method, the method involving the use of Woodward's reagent K, carbodiimidazole method, reduction-oxidation method and DCC/HONB method may be mentioned. There are cases in which the NCA (N-carboxy-anhydride) method (the method involving the use of an intramolecular cyclic carbonyl compound corresponding to the amino acid without use of a protective group) may be utilized.

Prior to the condensation reaction, the carboxyl or/and amino group in starting material which will not be pertinent to the reaction may be previously protected or the carboxyl or/and amino groups of starting material which are pertinent to the reaction may be previously activated.

The protective groups for the starting material may be the protective groups mentioned hereinbefore. The carboxyl group of the starting material may also be protected in the form of metal salt (e.g. sodium salt, potassium salt), t-alkylamine salt (e.g. triethylamine salt, N-methylmorpholine salt) or ester (e.g. methyl ester, ethyl ester, benzyl ester, p-nitrobenzyl ester, t-butyl ester, t-amyl ester). As examples of the protective group for the amino group in the starting material, there may be mentioned benzyloxycarbonyl, t-butoxycarbonyl and isobornyloxycarbonyl. The imino group of histidine may be protected by benzyl, tosyl, 2,4-dinitrophenyl, t-butyloxycarbonyl and carbobenzoxy. The hydroxyl group of tyrosine may be protected in the ether form by benzyl and t-butyl.

As examples of the activated form of the carboxyl group in the starting material, there may be mentioned the corresponding acid anhydride, azide, active ester [i.e. esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, N-hydroxybenzotriazole)]. As an example of the activated form of the amino group in the starting material, there may be mentioned the corresponding phosphoric acid amide.

Assuming that the starting materials are A and B, the above combinations of carboxyl and amino groups in starting materials may be as shown in the following table.

| Combination | Starting materials | | | |
|---|---|---|---|---|
| | A | | B | |
| Example | COOH | NH$_2$ | COOH | NH$_2$ |
| 1* | Free | Protected | Protected | Free |
| 2 | Activated | Protected | Free | Free |
| 3 | Free | Protected | Protected | Activated |

Note: In the case of *, a dehydrating agent (e.g. a carbodiimide reagent such as dicyclohexylcarbodiimide) is desirably present in the reaction system.

The reaction may be carried out in a solvent. This solvent is selected from among the solvents hitherto-known to be suited for peptide synthesis reactions. Thus, for example, there may be mentioned anhydrous or aqueous dimethylformamide, dimethylsulfoxide, pyridine, chloroform, dioxane, dichloromethane and tetrahydrofuran as well as appropriate mixtures of such solvents.

The reaction temperature is selected from the range hitherto-known to be suited for peptide synthesis reactions and may normally range from about $-20°$ C. to $30°$ C. The precursor compounds (protected peptides) for the compounds of this invention may be easily produced as well by the solid-phase synthesis procedure.

The protected compound of formula (II) so obtained is subjected to a deprotecting reaction by which the protective groups are removed. While the deprotecting reaction depends on the type of protective group involved, it is preferred for commercial purposes that this reaction is such that it removes all the protective groups in a single step without affecting the peptide bonds. Thus, protective groups are chosen in consideration of this possibility. Table 1 shows some combinations of different types of protective groups and typical deprotecting conditions.

TABLE 1

| Conditions | Protective group | |
|---|---|---|
| of removal | $Y_1$ | $Y_2$ |
| H$_2$/catalyst | Z | Bzl |
| H$_2$/catalyst | Z | — |
| CF$_3$COOH | BOC | Bu$^t$ |
| 2N—HCl | BOC | — |
| (in acetic acid) | | |
| CH$_3$SO$_3$H | Z | — |

While Table 1 is a listing of some deprotecting reactions such as catalytic reduction involving the use of palladium black, palladium-on-carbon, platinum or the like catalyst and acid hydrolysis with trifluoroacetic acid, dilute hydrochloric acid or methanesulfonic acid, such other processes as reduction with sodium metal in liquid ammonia and acid hydrolysis with the use of trifluoromethanesulfonic acid, a solution of hydrogen bromide in glacial acetic acid, hydrogen fluoride or the like may also be mentioned. These reactions are generally conducted at suitable temperatures from $-20°$ C. to $40°$ C., and in the case of acid hydrolysis, the addition of a cation acceptor such as anisole, phenol or thioanisole is advantageous.

In the production of the tetrapeptide acylhydrazide (I), the introduction of D-methioninesulfoxide may be conducted by the following manners.

For example, (1) D-methionine sulfoxide is used as the starting material, (2) an intermediate of the compound (III) representable by the formula (III)

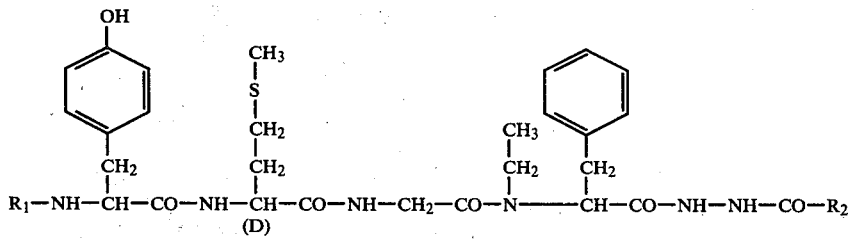

(III)

wherein $R_1$ and $R_2$ have the same meaning as defined above; is oxidized, and then the resulting compound is subjected to peptide synthesis, or (3) the compound (III) is subjected to oxidation.

As examples of the oxidizing agent usable for the oxidation, there may be mentioned hydrogen peroxide, sodium perchloride, sodium perborate, chloramine T, tribromocresol, N-chlorosuccinimide and chloroauric acid.

The amount of the oxidizing agent is usually not less than about 1 equivalent, preferably about 1 to 10 equivalent to the compound (III).

The solvent usable for the reaction is, for example, water, acetic acid, alcohol (e.g. methylalcohol, ethylalcohol), or mixtures thereof. The reaction temperature is generally $-20°$ C. to $40°$ C.

After completion of the reaction, the peptide derivative (I) so produced is isolated by procedures which are known for the separation of peptide derivatives, i.e. by extraction, distribution, reprecipitation, recrystallization or column chromatography.

The peptide (I) may be obtained in the form of a salt, e.g. the organic acid salt or inorganic acid salt, preferably acetate, citrate, tartrate, hydrochloride or sulfate.

The following is the result of a pharmacological test with the compound (I) of this invention.

Phenylquinone writhing method

The compound (I) of the present invention was administered orally or subcutaneously to Slc:ICR mice weighing 18–20 g. According to the method of E. Siegmund, R. Cadmus and G. Lu [Proc. Soc.Exp.Biol, Med. 95, 729 (1957)], 0.02% phenylquinone in 5% ethanol saline was injected intraperitoneally in a dose of 0.1 ml/10 g body weight 30 min. after administration of the compound (I). The frequency of abdominal writhing was then counted for 20 min. Analgesic effect was indicated by comparing test group with control group.

In the above test, the compound (H-Tyr-(D)-Met(O)-Gly-EtPhe-NHNHCOCH$_3$) was effective in a small dose of 0.078 mg/1 kg body weight by oral rout. This fact indicates that analgesic activity of the compound (I) is about 32 times higher than that (2.5 mg/kg) of morphine, which is regarded as a representative analgesic.

Moreover, in the case of subcutaneous rout, analgesic activity of the compound (I) is about 700 times higher than that of morphine.

The compound (I) of this invention further has a strong gastrointestinal motility inhibitory activity and is, therefore, useful as a drug for the treatment of gastrointestinal disturbances such as diarrhea.

Therefore, the compound (I) and its pharmacologically acceptable salts can for instance be used as analgesics for the relief of pains inclusive of the pain of advanced-stage cancer and as medicaments for the treatment of gastrointestinal disorders such as diarrhea, in mammalian animals such as mouse, rat, rabbit, dog, monkey and human being etc. or be used as medicaments for the treatment of mental diseases such as schizophrenia.

The compound (I) and its pharmacologically acceptable salts, which are provided by this invention, are extremely low in toxicity and no death is encountered even at the dose level of 100 mg/kg which is by far beyond the effective dose.

The compound of this invention may be administered in its free form or as a suitable salt thereof. In the case of free compound (I), the proper dosage is generally in the range of 0.001 to 20 mg/kg. The dosage of the salt of (I) may also range generally from 0.001 to 20 mg/kg, as free compound (I). The compound and its salts according to this invention are mainly administered by oral, rectal, intravenous or subcutaneous route. Particularly useful is continuous infusion or instillation in the course of a surgical operation.

Useful dosage forms include tablets, powder injections, suppositories, nasal use and so forth, although instillable preparations are also useful. Being stable substances, the compounds according to this invention can be stored as dissolved in physiological saline but they may be provided in the form of lyophilized ampoule preparations as compounded with mannitol or sorbitol for extemporaneous dissolution and use.

Like compound (I), several species of the compound (II) and (III) also have analgesic activity.

The following examples are given to describe this invention in further detail. It should be understood that the Sephadex LH-20 used for the purification of final products is the product of Pharmacia (Sweden) and that the purity of each compound prepared was assayed by thin-layer chromatography on Kieselgel 60F-254, Merck A. G. (West Germany), using the following solvent systems:

$Rf^1$: chloroform-methanol-acetic acid (9:1:0.5)

$Rf^2$: ethyl acetate-pyridine-acetic acid-water (60:20:6:10)

EXAMPLE 1

Production of H-Tyr-(D)-Met(O)-Gly-EtPhe-NHNHCOCH$_3$ (I) Production of Z-EtPhe-NHNHCOCH$_3$ In 30 ml of DMF were dissolved 2.3 g of Z-EtPheOH and 0.78 g of NH$_2$NHCOCH$_3$, and the solution was cooled with ice. 1.40 g of HONB and 1.7 g of DCC were added to the solution, followed by stirring overnight. After the separated DCU was filtered out, the solvent was distilled off, and the residue was dissolved in a mixture of ethyl acetate-ether (1:1). The solution was washed with 1 N aqueous ammonia and dried over anhydrous sodium sulfate. Distilling off of the solvent provided an oily substance. Yield of 2.4 g (oil), Rf[1] 0.63.

(II) Production of BOC-Tyr-(D)-Met-Gly-EtPhe-NHNHCOCH$_3$

In 50 ml of MeOH was dissolved 2.8 g of Z-EtPhe-NHNHCOCH$_3$ and catalytic reduction was carried out in the presence of palladium black. The catalyst was filtered out and the solvent was distilled off. The residue was dissolved in 30 ml of DMF, and 3.0 g of BOC-Tyr-(D)-Met-GlyOH and 1.0 g of HOBt were added to the solution, which was then cooled with ice. 1.5 g of DCC was added to the solution, followed by stirring overnight. The separated DCU was filtered out, and the solvent was distilled off. The residue was dissolved in ethyl acetate, and the solution was washed with 10% aqueous citric acid solution and 1 N aqueous ammonia, successively, then concentrated, and chromatographed on a column of silica gel (3.6×8 cm). The elution was carried out with 5% MeOH/chloroform, and the fractions of 220 to 420 ml were collected and concentrated. The residue was treated with ether and collected by filtration as powder. Yield: 0.39 g, melting point, 97°–101° C., $[\alpha]_D^{24}$ −9.7° (c=0.79, DMF), Rf[1] 0.42.

Elemental analysis, for $C_{24}H_{48}O_8N_6S$: Calcd. (%): C, 58.26; H, 6.90; N, 11.99; S, 4.58; Found (%): C, 58.06; H, 6.94; N, 11.53; S, 4.54

(III) Production of BOC-Tyr-(D)-Met(O)-Gly-EtPhe-NHNHCOCH$_3$

In 2 ml of acetic acid was dissolved 0.29 g of BOC-Tyr-(D)-Met(O)-Gly-EtPhe-NHNHCOCH$_3$, and the solution was cooled, followed by adding 0.08 ml of 30% hydrogen peroxide. After the mixture was stirred for 10 minutes, ether was added to thereby recover by filtration the product in the form of powder. Yield: 0.27 g, melting point, 111°–113° C., $[\alpha]_D^{24}$ −12.5° (c=0.80, DMF), Rf[1] 0.20.

Elemental analysis, for $C_{34}H_{48}O_9N_6S \cdot H_2O$: Calcd. (%): C, 55.57; H, 6.86; N, 11.44; S, 4.37; Found (%): C, 55.30; H, 6.60; N, 11.28; S, 4.33

(IV) Production of H-Tyr-(D)-Met(O)-Gly-EtPhe-NHNHCOCH$_3$

To 0.20 g of BOC-Tyr-(D)-Met(O)-Gly-EtPhe-NHNHCOCH$_3$ were added 0.2 ml of anisole and 4 ml of TFA, and the mixture was shaken for 10 minutes. Then, the solvent was distilled off and ether was added to the residue of thereby recover by filtration the product in the form of powder. The product was subjected to ion exchange with Amberlite IRA 410 (acetic acid type) and then poured on a column (2.2×120 cm) of Sephadex LH-20. The elution was conducted with 0.1 N acetic acid, and the fractions of 285 to 340 ml were collected and lyophilized. Yield: 0.14 g, $[\alpha]_D^{24}$ +20.4° (c=0.50, MeOH), Rf[2] 0.22. Amino acid analysis (4% thioglycolic acid/6 N hydrochloric acid hydrolysis): Gly 0.99(1), Met 1.00(1), Tyr 1.04(1).

EXAMPLE 2

Production of
H-Tyr-(D)-Met(O)-Gly-EtPhe-NHNHCOCH$_2$CH$_3$ (I) Production of Z-EtPhe-NHNHCOCH$_2$CH$_3$ By the same procedure as in Example 1-(I), there was obtained the objective compound from 2.3 g of Z-EtPheOH and 0.81 g of NH$_2$NHCOCH$_2$CH$_3$. Yield of 2.5 g (oil), Rf[1] 0.65.

(II) Production of BOC-Tyr-(D)-Met-Gly-EtPhe-NHNHCOCH$_2$CH$_3$

By the same procedure as in Example 1-(II), there was obtained the objective compound from 2.4 g of Z-EtPhe-NHNHCOCH$_2$CH$_3$ and 2.4 g of BOC-Tyr-(D)-Met-Gly-OH. Yield: 2.9 g, melting point, 95°–100° C., $[\alpha]_D^{24}$ −8.5° (c=1.00, DMF), Rf[1] 0.45.

Elemental analysis, for $C_{35}H_{50}O_8N_6S$: Calcd. (%): C, 58.80; H, 7.05; N, 11.76; S, 4.49; Found (%): C, 58.43; H, 6.97; N, 11.55; S, 4.70.

(III) Production of BOC-Tyr-(D)-Met(O)-Gly-EtPhe-NHNHCOCH$_2$CH$_3$

By the same procedure as in Example 1-(III), there was obtained the objective compound from 1.0 g of BOC-Tyr-(D)-Met-Gly-EtPhe-NHNHCOCH$_2$CH$_3$. Yield: 0.93 g, melting point, 104°–109° C., $[\alpha]_D^{24}$ −10.4° (c=0.95, DMF), Rf[1] 0.22.

Elemental analysis, for $C_{35}H_{50}O_9N_6S \cdot H_2O$: Calcd. (%): C, 56.13; H, 7.00; N, 11.22; S, 4.28; Found (%): C, 55.85; H, 6.95; N, 11.03; S, 4.05

(IV) Production of H-Tyr-(D)-Met(O)-Gly-EtPhe-NHNHCOCH$_2$CH$_3$

To 0.50 g of BOC-Tyr-(D)-Met(O)-Gly-EtPhe-NHNHCOCH$_2$CH$_3$ were added 0.5 ml of anisole and 5 ml of TFA, and the mixture was shaken for 10 minutes. The solvent was distilled off, and ether was added to recover by filtration the product in the form of powder. The product was subjected to ion exchange on Amberlite IRA 410 (acetic acid type), and then poured on a column (2.2×120 cm) of Cephadex LH-20. The elution was conducted with 0.1 N acetic acid, and the fractions of 300 to 350 ml were collected and lyophilized. Yield: 0.35 g $[\alpha]_D^{24}$ +18.5° (c=0.49, MeOH), Rf[2], 0.24. Amino Acid analysis (4% thioglycolic acid/6 N hydrochloric acid hydrolysis): Gly 1.00(1), Met 1.05(1), Tyr 0.97(1).

EXAMPLE 3

Production of
H-Tyr-(D)-Met(O)-Gly-EtPhe-NHNHCOCH$_2$CH$_2$CH$_3$ (I) Production of Z-EtPhe-NHNHCOCH$_2$CH$_2$CH$_3$ By the same procedure as in Example 2-(I), there was obtained the objective compound from 2.3 g of Z-EtPheOH and 0.84 g of NH$_2$NHCOCH$_2$CH$_2$CH$_3$. Yield: 2.4 g (oil), Rf[1] 0.67.

(II) Production of BOC-Tyr-(D)-Met-Gly-EtPhe-NHNHCOCH$_2$CH$_2$CH$_3$

By the same procedure as in Example 2-(II), there was obtained the objective compound from 1.5 g of Z-EtPhe-NHNHCOCH$_2$CH$_2$CH$_3$ and 1.4 g of BOC-Tyr-(D)-Met-Gly-OH. Yield: 1.8 g, melting point, 89°–94° C., $[\alpha]_D^{24}$ −7.7° (c=1.00, DMF), Rf[1] 0.48.

Elemental analysis, for $C_{36}H_{52}O_8N_6S$: Calcd. (%): C, 59.32; H, 7.19; N, 11.53; S, 4.40; Found (%): C, 59.58; H, 7.07; N, 11.41; S, 4.18

(III) Production of BOC-Tyr-(D)-Met(O)-Gly-EtPhe-NHNHCOCH$_2$CH$_2$CH$_3$

By the same procedure as in Example 2-(III), there was obtained the objective compound from 1.0 g of BOC-Tyr-(D)-Met-Gly-EtPhe-NHNHCOCH$_2$CH$_2$CH$_3$. Yield: 0.97 g, melting point, 106°–110° C., $[\alpha]_D^{24}$ −11.3° (c=0.93, DMF).

Elemental analysis, for $C_{36}H_{52}O_9N_6S \cdot H_2O$: Calcd. (%): C, 56.67; H, 7.13; N, 11.02; S, 4.20; Found (%): C, 56.35; H, 6.97; N, 10.86; S, 3.92

(IV) Production of H-Tyr-(D)-Met(O)-Gly-EtPhe-NHNHCOCH$_2$CH$_2$CH$_3$

By the same procedure as in Example 2-(IV), there was obtained the objective compound from 0.50 g of BOC-Tyr-(D)-Met(O)-Gly-EtPhe-NHNHCOCH$_2$CH$_2$CH$_3$. Yield: 0.29 g, $[\alpha]_D^{24}+17.6°$ (c=0.52, MeOH), Rf$^2$ 0.26. Amino acid analysis (4% thioglycolic acid/6 N hydrochloric acid hydrolysis): Gly 1.00(1), Met 1.03(1), Tyr 0.98(1).

EXAMPLE 4

Production of H-Tyr-(D)-Met(O)-Gly-EtPhe-NHNHCOCH$_3$.½ sulfate

In 2 ml of methanol was dissolved 70 mg of H-Tyr-(D)-Met(O)-Gly-EtPhe-NHNHCOCH$_3$ as obtained in Example 2, and 1 ml of 1/10 N sulfuric acid was added to the solution. The methanol was distilled off, followed by the lyophilization. Yield: 73 mg. The same procedure conducted with the compounds of Examples 1, 3 and 4 produced the corresponding sulfates, respectively.

EXAMPLE 5

Preparation formulated for tablets

| Peptide (as produced in Example 1): | 10 mg |
|---|---|
| Corn starch: | 20 mg |
| Lactose: | 80 mg |
| Gelatin: | 2 mg |
| Magnesium stearate: | 2 mg |

The peptide, corn starch and lactose were mixed, and the mixture, with use of aqueous gelatin solution, was processed in the form of granules and dried. Magnesium stearate was added to the granules, which were then compressed into tablets.

EXAMPLE 6

Preparation formulated for injections

| Peptide (as produced in Example 1); | 0.5 mg |
|---|---|
| Sorbitol: | 100 mg |

Sorbitol and the peptide were mixed, and the mixture was placed in a vial, followed by sealing. The preparation, in the event of its use, is admixed with 2 ml of distilled water to be used as an injection solution.

EXAMPLE 7

Preparation formulated for suppositories

| Peptide (as produced in Example 2): | 3 mg |
|---|---|
| Witepsol: | 2 g |

The peptide and Witepsol were heated at 40° C. for melting to disperse the peptide. The mixture was then molded into a suppository.

EXAMPLE 8

Preparation formulated for nasal application

| Peptide (as produced in Example 3): | 3 mg |
|---|---|
| Chlorobutanol: | 2.5 mg |

The peptide and chlorobutanol were dissolved in physiological saline to make a total volume of 0.5 ml, thereby producing a preparation for nasal application.

What we claim is:

1. A compound of the formula:

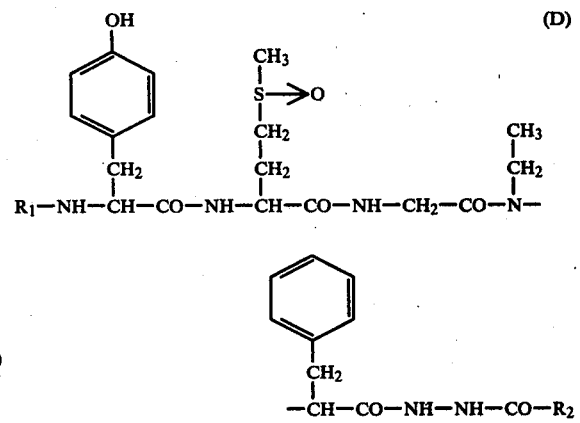

wherein R$_1$ is hydrogen or methyl, R$_2$ is lower alkyl; or a pharmacologically acceptable acid addition salt thereof.

2. The compound as claimed in claim 1, wherein R$_1$ is hydrogen.

3. The compound as claimed in claim 1, wherein R$_2$ is alkyl having 1 to 5 carbon atoms.

4. The compound as claimed in claim 1, R$_2$ is methyl.

5. The compound as claimed in claim 1, R$_2$ is ethyl.

6. The compound as claimed in claim 1, R$_2$ is propyl.

7. The compound as claimed in claim 1, R$_1$ is hydrogen and R$_2$ is methyl.

8. The compound as claimed in claim 1, R$_1$ is hydrogen and R$_2$ is ethyl.

9. The compound as claimed in claim 1, R$_1$ is hydrogen and R$_2$ is propyl.

10. A pharmaceutical composition for pain-relieving in mammalian animals, which contains an effective amount of a compound of the formula:

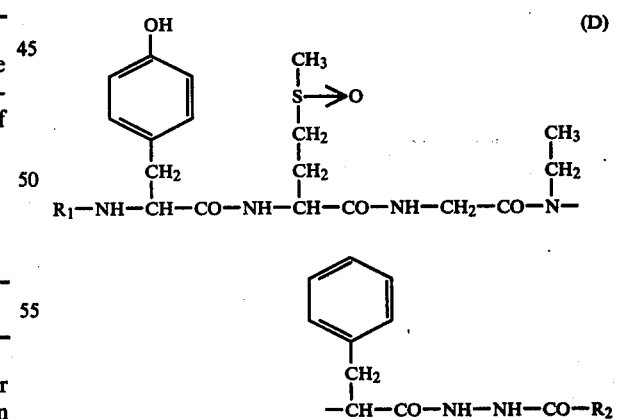

wherein R$_1$ is hydrogen or methyl, R$_2$ is lower alkyl; or a pharmacologically acceptable acid addition salt thereof, and a pharmacologically acceptable carrier.

11. The composition as claimed in claim 10, which is in the form of tablet, powder or nasal use.

12. The composition as claimed in claim 10, which is in the form of injection.

* * * * *